United States Patent [19]

Hare

[11] Patent Number: Plant 5,547

[45] Date of Patent: Sep. 3, 1985

[54] RED DELICIOUS APPLE TREE-HARED CULTIVAR

[75] Inventor: Bruner Hare, Long Creek, S.C.

[73] Assignee: Stark Brothers Nurseries and Orchards Company, Louisiana, Mo.

[21] Appl. No.: 494,551

[22] Filed: May 13, 1983

[51] Int. Cl.[3] ..... A01H 5/03

[52] U.S. Cl. ..... Plt./35

[58] Field of Search ..... Plt./35

*Primary Examiner*—Robert E. Bagwill

*Attorney, Agent, or Firm*—Burns, Doane, Swecker & Mathis

[57] ABSTRACT

A new and distinct spur-type Red Delicious apple variety is provided which originated as a limb mutation of the apple tree of U.S. Plant Pat. No. 2,816. Unlike its parent cultivar, the fruit of the new variety colors approximately 15 to 20 days earlier, is roundly conical in configuration, and exhibits a solid dark red blush with no stripes. The fruit of the new variety resembles closely that of the variety of U.S. Plant Pat. No. 3,025, but differs therefrom in that it is free from russet. Also, the fruit of the new variety colors more fully earlier in the season than that of the varieties of U.S. Plant Pat. Nos. 1,565, 1,916, and 3,578.

1 Drawing Figure

SUMMARY OF THE INVENTION

The new and distinct variety was discovered by me in July of 1975 as a bud or limb mutation growing on a five year old Red Delicious apple tree of U.S. Plant Pat. No. 2,816. Such parent variety is being marketed under the OREGON SPUR trademark. The limb mutation was found in a five year old block of Red Delicious apple trees of U.S. Plant Pat. No. 2,816 growing in my orchard at Long Creek, Oconee County, S.C. 29658. Other Red Delicious cultivars were also present in my orchard.

At the time of the discovery I noticed that the fruit borne on a single limb of a single tree had colored to a complete or solid dark red blush while the other fruit on the same tree had only faint red stripes characteristic of the variety of U.S. Plant Pat. No. 2,816. I marked the unusual limb so that I could continue to observe it as the season progressed and during subsequent seasons. I also propagated the new variety into other trees in my orchard for observation.

My continued observation of the original sport limb and its progeny have convinced me that a new and distinct variety has been discovered. The new variety exhibits a spur-type growth habit similar to that of the parent variety. It yields fruit which is rounder in shape than the parent. For instance, the fruit of the parent variety can be considered to be conic while that of the present new variety is roundly conical. The fruit colors approximately 15 to 20 days earlier than that of its parent. Also, this coloration is a solid dark red blush which lacks the stripes which are exhibited by its parent.

The fruit of the new variety is similar in size, shape, and color to that of the Matson cultivar of U.S. Plant Pat. No. 3,025. However, the Matson cultivar is not of the spur-type as is the new variety and lacks russet resistance as does the new variety. Such Matson cultivar has been marketed under the STARK and EARLIBRITE trademarks. The russet resistance of the new variety has been found to be particularly advantageous when grown in the Southeastern fruit region of the United States.

The fruit of the new variety has been found to consistently color earlier in the season than the following Red Delicious varieties when grown at the same location:

(a) Bisbee cultivar of U.S. Plant Pat. No. 1,565 which has been marketed under the STARKRIMSON trademark, (b) Hutchinson cultivar of U.S. Plant Pat. No. 1,916 which has been marketed under the TOPRED trademark, and (c) Campbell cultivar of U.S. Plant Pat. No. 3,578 which has been marketed under the REDCHIEF trademark.

Asexual propagation as early as 1976 and subsequent testing by me at Long Creek, Oconee County, S.C. 29658 has demonstrated that the unique combination of characteristics of the new variety comes true to form and is established and is transmitted through suceeding propagations. All specimens described herein were grown at Long Creek, S.C.

The new variety has been named the Hared cultivar and is being marketed by the Stark Brothers Nurseries and Orchards Company under the DIXIERED and STARKSPUR trademarks.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF THE NEW VARIETY

The following is a detailed description of the new variety where color terminology is to be accorded its ordinary dictionary significance except where otherwise indicated. The specimens described were grown at Long Creek, Oconee County, S.C. 29658.

Representative dates of first and last picking at this location were Aug. 10, 1980 and Aug. 25, 1980.

Tree: Medium small; medium vigorous; upright; dense; medium slow growing; hardy; very productive; regular bearing.

*Trunk.*—Stocky; smooth.

*Branches.*—Medium thick; smooth; little branching; many spurs on limbs; brown — Diamine Brown Plate XIII — Color No. 3′ tone m of Ridgeway Color Standards and Nomenclature.

*Lenticels.*—Medium few; medium small.

*Leaves.*—Medium large; medium narrow; medium long; ovate; taper pointed; thick; dark green; Bluish Gray Green Plate XLIII — Color No. 41‴ of Ridgeway Color Standards and Nomenclature; rugose. Length. — Approximately $3\frac{3}{4}$ to 4 inches. Width. — Approximately $1\frac{1}{2}$ inches. Margin. — Coursely serrate. Petiole. — Medium long approximately 1 to $1\frac{1}{4}$ inches; thick.

Flowers: Medium early; large; white — edges tinged with Carmine — plate 21/3 p 21 Vol. 1 of Horticultural Color Guide.

*Date of first bloom.*—April 10th.

*Date of full bloom.*—April 14th.

Fruit:

*Maturity when described.*—Hard ripe; date — Aug. 10, 1980.

*Size.*—Uniform. Axial diameter. — Approximately $3\frac{3}{8}$ inches. Transverse in suture planes. — Approximately 3 to $3\frac{1}{4}$ inches.

*Form.*—Globose; conical; angular.

*Cavity.*—Symmetrical; flaring toward apex; pubescent toward apex. Depth. — Approximately $\frac{5}{8}$ inch. Breadth. — Approximately $1\frac{3}{8}$ inch. Markings. — Deep Grape Green Plate XLI color No. 25‴ tone i of Ridgeway Color Standards and Nomenclature.

*Basin.*—Symmetrical; abrupt at base; base wide; undulate; glabrous. Depth. — Approximately $\frac{3}{8}$ inch. Breadth. — Approximately $1\frac{1}{8}$ inch. Markings. — None.

*Stem.*—Clubbed; stout; pubescent. Length. 13 Approximately $\frac{7}{8}$ to 1 inch. Breadth. — Approximately $\frac{1}{8}$ inch. Markings. — None.

*Calyx.*—Closed; persistent; broadly lanceolate; acute. Length. — Approximately $\frac{1}{4}$ inch; approximate; prostrate; reflexed from base at apex; converged from base toward center. Outer-surface. — Pubescent. Inter-surface. — Pubescent.

*Eye.13* Medium small; closed.

*Skin.*—Thick, tough; smooth; waxed. Dots. — Obscure; many; small; even; circular. Color of Dots. — White. Distribution of dots. — Overall; most numerous toward base. Ground color. — Rose Pink Plate XII Color No. 71 — Tone F of Ridgeway Color Standards and Nonmenclature.

Color of markings. — Blushed; self-colored; dull; Eugenia Red Plate XIII Color No. 1′ of Ridgeway Color Standards and Nomenclature. Bloom. — Scant. Scarfskin. — Wanting. General color effect. — Nearly solid dark red.

*Flesh.*—Juicy. Color. 13 Satiny white with greenish tint. Texture. — Firm; fine; crisp. Flavor. — Mild aroma; wanting. Quality. — Good.

*Core.*—Medium. Bundle area. — Medium small; broadly oblate; symmetrical; acute at base; halves of area equal. Bundle color. — Light green; inconspicuous; in one whorl. Core lines. — Clasping; in cross-section; indistinct. Carpellary area. — Indistinct; large. Calyx tube. — Glabrous toward base; apex. Stem of funnel. — Short. Depth of tube to shoulder. — Approximately 5/16 inch. Entire depth. — Approximately 7/16 inch. Styles. — Present; distinct toward base; pubescent toward base. Stamens. — in one distinct whorl; marginal. Seed cells. — Axile; open. Cell walls. — Approximate; thin; tough. Length. — Approximately 9/16 inch. Breadth. — Approximately 5/16 inch. Longitudinal section. — Broadly ovate; obtuse at apex. Surface. — Tufted. Cross Section. — Broad.

*Seeds.*—Number perfect — 7; number imperfect — 1. Number in one cell. — 2. Length. — Approximately 5/16 inch. Breadth. — Approximately 3/16 inch. Form. — Acute. Color. — Brown.

Use:

*Market.*—Dessert.

Keeping quality: Good.

Number of days in ordinary storage: Approximately 120 days.

Resistance to:

*Insects.*—Medium.

*Diseases.*—Medium.

I claim:

1. A new and distinct variety of Red Delicious apple tree, substantially as illustrated and described, characterized by (a) a spur-type tree growth habit similar to the variety of U.S. Plant Pat. No. 2,816, (b) the ability to form roundly conical fruit having a solid dark red blush which is similar to that of U.S. Plant Pat. No. 3,025 in size, shape, and color with the exception that such new and distinct variety is russet resistant, and (c) the ability to form fruit which colors earlier in the season than the varieties of U.S. Plant Pat. Nos. 1,565, 1,916, and 3,578.

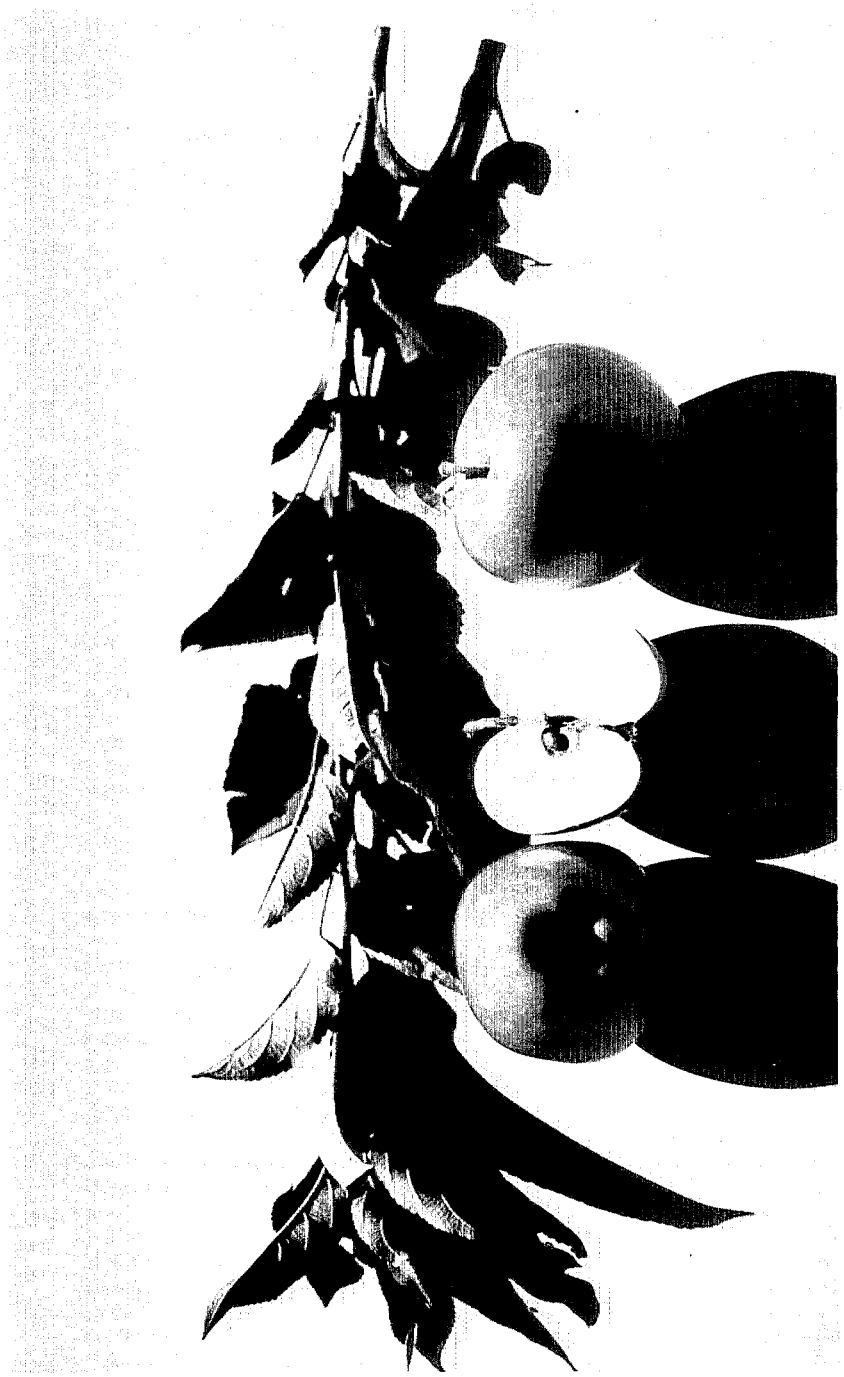

* * * * *